(12) United States Patent
Kshirsagar

(10) Patent No.: US 9,029,100 B2
(45) Date of Patent: May 12, 2015

(54) MICROORGANISM CONCENTRATION PROCESS AND CONCENTRATION AGENT FOR USE THEREIN

(75) Inventor: Manjiri T. Kshirsagar, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 137 days.

(21) Appl. No.: 13/511,169

(22) PCT Filed: Dec. 17, 2010

(86) PCT No.: PCT/US2010/060947
§ 371 (c)(1),
(2), (4) Date: Jul. 17, 2012

(87) PCT Pub. No.: WO2011/079038
PCT Pub. Date: Jun. 30, 2011

(65) Prior Publication Data
US 2012/0276580 A1 Nov. 1, 2012

Related U.S. Application Data

(60) Provisional application No. 61/289,213, filed on Dec. 22, 2009.

(51) Int. Cl.
| | | |
|---|---|---|
| *B01J 20/32* | (2006.01) | |
| *C12N 1/02* | (2006.01) | |
| *G01N 1/40* | (2006.01) | |
| *B01J 20/10* | (2006.01) | |
| *B01J 20/06* | (2006.01) | |
| *B01J 20/14* | (2006.01) | |
| *B01J 20/30* | (2006.01) | |
| *B01J 20/04* | (2006.01) | |

(52) U.S. Cl.
CPC *C12N 1/02* (2013.01); *G01N 1/405* (2013.01); *B01J 20/10* (2013.01); *B01J 20/06* (2013.01); *B01J 20/14* (2013.01); *B01J 20/3071* (2013.01); *B01J 20/041* (2013.01); *B01J 20/3204* (2013.01); *B01J 20/3236* (2013.01)

(58) Field of Classification Search
USPC ................................ 435/34, 176; 252/184
See application file for complete search history.

(56) References Cited

U.S. PATENT DOCUMENTS

| | | | | |
|---|---|---|---|---|
| 3,475,375 A | * | 10/1969 | Yates | ........................... 525/472 |
| 4,560,660 A | | 12/1985 | Geinaert | |
| 4,668,648 A | | 5/1987 | Strack | |
| 5,139,760 A | | 8/1992 | Ogawa | |
| 5,403,799 A | * | 4/1995 | Miller et al. | ..................... 502/64 |
| 5,569,634 A | * | 10/1996 | Miller et al. | ..................... 502/64 |
| 8,524,261 B2 | | 9/2013 | Schmidt et al. | |
| 2010/0190171 A1 | * | 7/2010 | Kshirsagar et al. | ............... 435/6 |
| 2010/0209961 A1 | * | 8/2010 | Kshirsagar et al. | ............. 435/29 |
| 2012/0034621 A1 | * | 2/2012 | Kshirsagar et al. | ............ 435/7.1 |
| 2013/0029324 A1 | * | 1/2013 | Rajagopal et al. | ............. 435/6.1 |
| 2013/0260370 A1 | * | 10/2013 | Kshirsagar et al. | ............... 435/5 |

FOREIGN PATENT DOCUMENTS

| | | |
|---|---|---|
| EP | 0 253 663 | 1/1988 |
| EP | 0603989 | 11/1999 |
| EP | 2 316 891 | 10/2010 |
| JP | H05-78118 | 3/1993 |
| WO | WO 2009/046191 | 4/2009 |
| WO | WO 2009/085357 | 7/2009 |

OTHER PUBLICATIONS

Farrah et al., "Adsorption of viruses by diatomaceous earth coated with metallic oxides and metallic peroxides", *Wat. Sci. Tech.*, vol. 24, No. 2, p. 235-240, 1991.

Farrah et al., "Use of modified diatomaceous earth for removal and recovery of viruses in water", *Applied and Environmental Microbiology*, Sep. 1991, vol. 57, No. 9, p. 2502-2506.

Farrah et al., "Adsorption of viruses to diatomaceous earth modified by in-situ precipitation of metallic salts," *Zeit fu Ges Hyg*, 34(1988), Heft 9, p. 520-521.

Krysztafkiewicz, "Amorphous 12,14,15 magnesium silicate—synthesis, physicochemical properties and surface morphology", *Advanced Powder Technology*, vol. 15, No. 5, (2004) pp. 549-565.

* cited by examiner

*Primary Examiner* — Ralph Gitomer
(74) *Attorney, Agent, or Firm* — Adrian L. Pishko; Adam Bramwell; Stephen L. Crooks

(57) ABSTRACT

A process is provided for capturing or concentrating microorganisms for detection or assay. The process includes providing an adsorption buffer-modified inorganic concentration agent, providing a sample including at least one microorganism strain, and contacting the adsorption buffer-modified inorganic concentration agent with the sample such that at least a portion of the at least one microorganism strain is bound to or captured by the adsorption buffer-modified inorganic concentration agent. The adsorption buffer-modified inorganic concentration agent is prepared by a process including contacting at least one inorganic concentration agent with at least one cation-containing salt solution, so as to wet at least a portion of the inorganic concentration agent, and drying the resulting wet inorganic concentration agent.

15 Claims, No Drawings

MICROORGANISM CONCENTRATION PROCESS AND CONCENTRATION AGENT FOR USE THEREIN

CROSS REFERENCE TO RELATED APPLICATIONS

This application is a national stage filing under 35 U.S.C. 371 of PCT/US2010/060947, filed Dec. 17, 2010, which claims priority to U.S. Provisional Application No. 61/289,213, filed Dec. 19, 2009, the disclosure of which is incorporated by reference in its/their entirety herein.

FIELD

This invention relates to processes for capturing or concentrating microorganisms such that they remain viable for detection or assay. In other aspects, this invention also relates to processes for preparing concentration agents for use in carrying out such concentration processes (as well as to the resulting concentration agents and to diagnostic kits comprising the resulting concentration agents).

BACKGROUND

Food-borne illnesses and hospital-acquired infections resulting from microorganism contamination are a concern in numerous locations all over the world. Thus, it is often desirable or necessary to assay for the presence of bacteria or other microorganisms in various clinical, food, environmental, or other samples, in order to determine the identity and/or the quantity of the microorganisms present.

Bacterial DNA or bacterial RNA, for example, can be assayed to assess the presence or absence of a particular bacterial species even in the presence of other bacterial species. The ability to detect the presence of a particular bacterium, however, depends, at least in part, on the concentration of the bacterium in the sample being analyzed. Bacterial samples can be plated or cultured to increase the numbers of the bacteria in the sample to ensure an adequate level for detection, but the culturing step often requires substantial time and therefore can significantly delay the assessment results.

Concentration of the bacteria in the sample can shorten the culturing time or even eliminate the need for a culturing step. Thus, methods have been developed to isolate (and thereby concentrate) particular bacterial strains by using antibodies specific to the strain (for example, in the form of antibody-coated magnetic or non-magnetic particles). Such methods, however, have tended to be expensive and still somewhat slower than desired for at least some diagnostic applications.

Concentration methods that are not strain-specific have also been used (for example, to obtain a more general assessment of the microorganisms present in a sample). After concentration of a mixed population of microorganisms, the presence of particular strains can be determined, if desired, by using strain-specific probes.

Non-specific concentration or capture of microorganisms has been achieved through methods based upon carbohydrate and lectin protein interactions. Chitosan-coated supports have been used as non-specific capture devices, and substances (for example, carbohydrates, vitamins, iron-chelating compounds, and siderophores) that serve as nutrients for microorganisms have also been described as being useful as ligands to provide non-specific capture of microorganisms.

Various inorganic materials (for example, hydroxyapatite and metal hydroxides) have been used to non-specifically bind and concentrate bacteria. Physical concentration methods (for example, filtration, chromatography, centrifugation, and gravitational settling) have also been utilized for non-specific capture, with and/or without the use of inorganic binding agents. Such non-specific concentration methods have varied in speed, cost (at least some requiring expensive equipment, materials, and/or trained technicians), sample requirements (for example, sample nature and/or volume limitations), space requirements, ease of use (at least some requiring complicated multi-step processes), suitability for on-site use, and/or effectiveness.

At least some of the non-specific concentration methods (for example, at least some of the methods utilizing inorganic binding agents) have involved the use of cation-containing adsorption buffers as additives to enhance microorganism binding. Such buffers have typically been used in liquid form (for example, in the form of aqueous salt solutions). Since on-site use of such buffers requires either the transport and handling of sterile liquids or on-site reconstitution of the buffers from dry salts under sterile conditions, the suitability of the adsorption buffers for on-site use has been somewhat limited.

SUMMARY

Thus, we recognize that there is an urgent need for processes for rapidly detecting pathogenic microorganisms. Such processes will preferably be not only rapid but also low in cost, simple (involving no complex equipment or procedures), and/or effective under a variety of conditions (for example, with varying types of sample matrices, varying bacterial loads, and varying sample volumes).

Briefly, in one aspect, this invention provides a process for non-specifically concentrating the strains of microorganisms (for example, strains of bacteria, fungi, yeasts, protozoans, viruses (including both non-enveloped and enveloped viruses), and bacterial endospores) present in a sample, such that the microorganisms remain viable for the purpose of detection or assay of one or more of the strains. The process comprises (a) providing an adsorption buffer-modified inorganic concentration agent, the adsorption buffer-modified inorganic concentration agent being prepared by a process comprising (1) contacting (preferably, by washing) at least one inorganic concentration agent (preferably, a particulate inorganic concentration agent) with at least one cation-containing salt solution (preferably, aqueous), so as to wet at least a portion of the inorganic concentration agent and (2) drying the resulting at least partially wet inorganic concentration agent (preferably, by heating to a temperature above about 25° C.); (b) providing a sample (preferably, in the form of a fluid) comprising at least one microorganism strain; and (c) contacting (preferably, by mixing) the adsorption buffer-modified inorganic concentration agent with the sample such that at least a portion of the at least one microorganism strain is bound to or captured by the adsorption buffer-modified inorganic concentration agent. The cation-containing salt solution preferably comprises at least one multivalent cation (more preferably, at least one divalent cation; most preferably, at least one divalent cation selected from divalent calcium cations, divalent magnesium cations, and combinations thereof).

Preferably, the concentration process further comprises detecting the presence of at least one bound microorganism strain (for example, by culture-based, microscopy/imaging, genetic, bioluminescence-based, or immunologic detection methods) and/or segregating (preferably, by gravitational settling) the resulting microorganism-bound concentration agent. The process can optionally further comprise separating the resulting segregated concentration agent from the sample.

The concentration process of the invention does not target a specific microorganism strain. Rather, it has been discovered that the capture or binding efficiency of relatively inexpensive, non-specific inorganic concentration agents surprisingly can be enhanced by a simple surface treatment method in which the agents are contacted with adsorption buffer solution and then dried. The resulting adsorption buffer-modified inorganic concentration agents can be at least somewhat more effective than their untreated counterparts in capturing a variety of microorganisms and, once prepared, can be used on site (in the field) without the need for transport and/or handling of sterile liquid buffer solutions or the need for on-site buffer solution reconstitution under sterile conditions. The adsorption buffer-modified inorganic concentration agents can be used to concentrate the microorganism strains present in a sample (for example, a food sample) in a non-strain-specific manner, so that one or more of the microorganism strains (preferably, one or more strains of bacteria) can be more easily and rapidly assayed.

The concentration process of the invention is relatively simple and low in cost (requiring no complex equipment or expensive strain-specific materials) and can be relatively fast (preferred embodiments capturing at least about 70 percent (more preferably, at least about 80 percent; most preferably, at least about 90 percent) of the microorganisms present in a sample in less than about 30 minutes, relative to a corresponding control sample without concentration agent). In addition, the process can be effective with a variety of microorganisms (including pathogens such as both gram positive and gram negative bacteria) and with a variety of samples (different sample matrices and, unlike at least some prior art methods, even samples having low microorganism content and/or large volumes). Thus, at least some embodiments of the process of the invention can meet the above-cited urgent need for low-cost, simple processes for rapidly detecting pathogenic microorganisms under a variety of conditions.

In another aspect, this invention provides a preferred concentration process comprising (a) providing an adsorption buffer-modified inorganic concentration agent, the adsorption buffer-modified inorganic concentration agent being prepared by a process comprising treating (for example, by contacting by any of various known or hereafter-developed methods of providing contact between two materials, including methods described herein including physical vapor deposition (PVD) techniques) at least one silicon-containing inorganic concentration agent with at least one adsorption buffer (salt or salt solution) comprising at least one cation, so as to provide silicon-containing inorganic concentration agent (preferably, in substantially dry or solvent-free form) having a surface composition having a ratio of atoms of the at least one cation (total of the cation atoms; see, for example, Table 4 below) to atoms of silicon that is greater than (preferably, at least about 50 percent greater than; more preferably, at least about 75 percent greater than; even more preferably, at least about 100 percent greater than; most preferably, at least about 200 or 300 percent greater than) that of the corresponding untreated silicon-containing inorganic concentration agent, as determined by X-ray photoelectron spectroscopy (XPS); (b) providing a sample comprising at least one microorganism strain; and (c) contacting the adsorption buffer-modified inorganic concentration agent with the sample such that at least a portion of the at least one microorganism strain is bound to or captured by the adsorption buffer-modified inorganic concentration agent. Useful physical vapor deposition (PVD) techniques include those described below (for example, in regard to metal deposition on diatomaceous earth).

In yet other aspects, the invention also provides two processes for preparing an adsorption buffer-modified inorganic concentration agent for use in carrying out the concentration process of the invention (as well as the modified agents prepared thereby and diagnostic kits comprising the modified agents), the adsorption buffer-modified inorganic concentration agent being prepared by a process comprising (a) contacting (preferably, by washing) at least one inorganic concentration agent (preferably, a particulate inorganic concentration agent) with at least one cation-containing salt solution (preferably, aqueous), so as to wet at least a portion of the inorganic concentration agent and (b) drying the resulting at least partially wet inorganic concentration agent (preferably, by heating to a temperature above about 25° C.); or, alternatively, the adsorption buffer-modified inorganic concentration agent being prepared by a process comprising treating (for example, by contacting by any of various known or hereafter-developed methods of providing contact between two materials, including methods described herein including physical vapor deposition (PVD) techniques) at least one silicon-containing inorganic concentration agent with at least one adsorption buffer (salt or salt solution) comprising at least one cation, so as to provide silicon-containing inorganic concentration agent (preferably, in substantially dry or solvent-free form) having a surface composition having a ratio of atoms of the at least one cation (total of the cation atoms; see, for example, Table 4 below) to atoms of silicon that is greater than (preferably, at least about 50 percent greater than; more preferably, at least about 75 percent greater than; even more preferably, at least about 100 percent greater than; most preferably, at least about 200 or 300 percent greater than) that of the corresponding untreated silicon-containing inorganic concentration agent, as determined by X-ray photoelectron spectroscopy (XPS); in each case with the proviso that the preparation process is carried out in the substantial absence of microorganism-containing sample (that is, prior to contacting the inorganic concentration agent with sample comprising at least one microorganism strain; thus, the inorganic concentration agent consists essentially of at least one inorganic material). Useful physical vapor deposition (PVD) techniques include those described below (for example, in regard to metal deposition on diatomaceous earth).

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

As used herein, the term "and/or" means one or all of the listed elements or a combination of any two or more of the listed elements.

The words "preferred" and "preferably" refer to embodiments of the invention that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a liquid sample suspected of containing "a" target microorganism can be interpreted to mean that the liquid sample can include "one or more" target microorganisms.

The above "Summary of the Invention" section is not intended to describe every embodiment or every implementation of the invention. The detailed description that follows more particularly describes illustrative embodiments. Throughout the detailed description, guidance is provided through lists of examples, which examples can be used in various combinations. In each instance, a recited list serves only as a representative group and should not be interpreted as being an exclusive list.

DEFINITIONS

As used in this patent application:
"concentration agent" means a material or composition that binds microorganisms (preferably, having a microorganism capture or binding efficiency of at least about 60 percent; more preferably, at least about 70 percent; even more preferably, at least about 80 percent; most preferably, at least about 90 percent);
"culture device" means a device that can be used to propagate microorganisms under conditions that will permit at least one cell division to occur (preferably, culture devices include a housing to reduce or minimize the possibility of incidental contamination and/or a source of nutrients to support the growth of microorganisms);
"detection" means the identification of at least a component of a microorganism, which thereby determines that the microorganism is present;
"genetic detection" means the identification of a component of genetic material such as DNA or RNA that is derived from a target microorganism;
"immunologic detection" means the identification of an antigenic material such as a protein or a proteoglycan that is derived from a target microorganism;
"microorganism" means any cell or particle having genetic material suitable for analysis or detection (including, for example, bacteria, yeasts, viruses, and bacterial endospores);
"microorganism strain" means a particular type of microorganism that is distinguishable through a detection method (for example, microorganisms of different genera, of different species within a genera, or of different isolates within a species);
"sample" means a substance or material that is collected (for example, to be analyzed);
"sample matrix" means the components of a sample other than microorganisms; and
"target microorganism" means any microorganism that is desired to be detected.

Inorganic Concentration Agent

General

Concentration agents suitable for use in carrying out the process of the invention include those inorganic materials or compositions that can bind microorganisms. Preferably, the inorganic concentration agents can capture or bind at least about 60 percent (more preferably, at least about 70 percent; even more preferably, at least about 80 percent; most preferably, at least about 90 percent) of the microorganisms present in a sample, relative to a corresponding control sample without concentration agent.

Suitable inorganic materials include metal oxides, metal silicates (for example, magnesium silicate), metal aluminosilicates, silica, metal carbonates (for example, calcium carbonate), metal phosphates (for example, hydroxyapatite), diatomaceous earth, surface-modified diatomaceous earth, and the like, and combinations thereof. If desired, particles bearing coatings of such inorganic materials can be used (for example, particles comprising magnetic cores with inorganic surface coatings).

Preferred inorganic materials include silicon-containing inorganic materials (for example, metal silicates, metal aluminosilicates, silica, diatomaceous earth, surface-modified diatomaceous earth, and the like, and combinations thereof) and combinations thereof. More preferred inorganic materials include metal silicates; metal aluminosilicates; silica; diatomaceous earth; metal oxide-, gold-, or platinum-modified diatomaceous earth; and combinations thereof. Metal oxide-modified (preferably, titanium dioxide- or ferric oxide-modified) diatomaceous earth, metal aluminosilicates, amorphous metal silicates (preferably, amorphous magnesium silicate; more preferably, amorphous, spheroidized magnesium silicate), and combinations thereof are even more preferred (with amorphous metal silicates and combinations thereof being still more preferred, and amorphous, spheroidized magnesium silicate being most preferred).

Preferably, the inorganic concentration agents are in particulate form, more preferably comprising microparticles. The microparticles preferably have a particle size in the range of about 1 micrometer (more preferably, about 2 micrometers; even more preferably, about 3 micrometers; most preferably, about 4 micrometers) to about 100 micrometers (more preferably, about 50 micrometers; even more preferably, about 25 micrometers; most preferably, about 20 micrometers); where any lower limit can be paired with any upper limit of the range.

Concentration or capture using the above-described concentration agents is generally not specific to any particular strain, species, or type of microorganism and therefore provides for the concentration of a general population of microorganisms in a sample. Specific strains of microorganisms can then be detected from among the captured microorganism population using any known optical detection method with strain-specific probes.

When dispersed or suspended in water systems, inorganic materials exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). Preferably, the inorganic concentration agents have a negative zeta potential at a pH of about 7.

Metal Silicates

Metal silicate concentration agents suitable for use in carrying out the process of the invention include amorphous silicates of metals such as magnesium, calcium, zinc, aluminum, iron, titanium, and the like (preferably, magnesium, zinc, iron, and titanium; more preferably, magnesium), and combinations thereof. Preferred are amorphous metal silicates in at least partially fused particulate form (more preferably, amorphous, spheroidized metal silicates; most preferably, amorphous, spheroidized magnesium silicate). Metal silicates are known and can be chemically synthesized by known methods or obtained through the mining and processing of raw ores that are naturally-occurring.

Amorphous, at least partially fused particulate forms of metal silicates can be prepared by any of the known methods of melting or softening relatively small feed particles (for example, average particle sizes up to about 25 micrometers) under controlled conditions to make generally ellipsoidal or spheroidal particles (that is, particles having magnified two-dimensional images that are generally rounded and free of sharp corners or edges, including truly or substantially circular and elliptical shapes and any other rounded or curved shapes). Such methods include atomization, fire polishing, direct fusion, and the like. A preferred method is flame fusion, in which at least partially fused, substantially glassy particles are formed by direct fusion or fire polishing of solid feed particles (for example, as in the method described in U.S. Pat. No. 6,045,913 (Castle), the description of which is incorporated herein by reference). Most preferably, such methods can be utilized to produce amorphous, spheroidized metal silicates by converting a substantial portion of irregularly-shaped feed particles (for example, from about 15 to about 99 volume percent; preferably, from about 50 to about 99 volume percent; more preferably, from about 75 to about 99 volume percent; most preferably, from about 90 to about 99 volume percent) to generally ellipsoidal or spheroidal particles.

Some amorphous metal silicates are commercially available. For example, amorphous, spheroidized magnesium silicate is commercially available for use in cosmetic formulations (for example, as 3M™ Cosmetic Microspheres CM-111, available from 3M Company, St. Paul, Minn.).

Amorphous metal silicate concentration agents can further comprise other materials including oxides of metals (for example, iron or titanium), crystalline metal silicates, other crystalline materials, and the like. The concentration agents, however, preferably contain essentially no crystalline silica.

Particularly preferred concentration agents suitable for use in carrying out the process of the invention include those that comprise an amorphous metal silicate and that have a surface composition having a metal atom to silicon atom ratio of less than or equal to about 0.5 (preferably, less than or equal to about 0.4; more preferably, less than or equal to about 0.3; most preferably, less than or equal to about 0.2), as determined by X-ray photoelectron spectroscopy (XPS). Such concentration agents include those described in U.S. Provisional Patent Application No. 60/977,180 (3M Innovative Properties Company), the descriptions of the concentration agents and methods of their preparation being incorporated herein by reference.

Preferably, the surface composition of the particularly preferred concentration agents also comprises at least about 10 average atomic percent carbon (more preferably, at least about 12 average atomic percent carbon; most preferably, at least about 14 average atomic percent carbon), as determined by X-ray photoelectron spectroscopy (XPS). XPS is a technique that can determine the elemental composition of the outermost approximately 3 to 10 nanometers (nm) of a sample surface and that is sensitive to all elements in the periodic table except hydrogen and helium. XPS is a quantitative technique with detection limits for most elements in the 0.1 to 1 atomic percent concentration range. Preferred surface composition assessment conditions for XPS can include a take-off angle of 90 degrees measured with respect to the sample surface with a solid angle of acceptance of ±10 degrees.

Such preferred metal silicate concentration agents can have zeta potentials that are more negative than that of, for example, a common metal silicate such as ordinary talc. Yet the concentration agents can be surprisingly more effective than talc in concentrating microorganisms such as bacteria, the surfaces of which generally tend to be negatively charged. Preferably, the concentration agents have a negative zeta potential at a pH of about 7 (more preferably, a Smoluchowski zeta potential in the range of about −9 millivolts to about −25 millivolts at a pH of about 7; even more preferably, a Smoluchowski zeta potential in the range of about −10 millivolts to about −20 millivolts at a pH of about 7; most preferably, a Smoluchowski zeta potential in the range of about −11 millivolts to about −15 millivolts at a pH of about 7).

Surface-Modified Diatomaceous Earth

Surface-modified diatomaceous earth concentration agents suitable for use in carrying out the process of the invention include those that comprise diatomaceous earth bearing, on at least a portion of its surface, a surface treatment comprising a surface modifier comprising metal oxide (preferably, titanium dioxide or ferric oxide), fine-nanoscale gold or platinum, or a combination thereof. Such concentration agents include those described in U.S. Provisional Patent Application No. 60/977,200 (3M Innovative Properties Company), the descriptions of the concentration agents and methods of their preparation being incorporated herein by reference. The surface treatment preferably further comprises a metal oxide selected from ferric oxide, zinc oxide, aluminum oxide, and the like, and combinations thereof (more preferably, ferric oxide). Although noble metals such as gold have been known to exhibit antimicrobial characteristics, the gold-containing concentration agents used in the process of the invention surprisingly can be effective not only in concentrating the microorganisms but also in leaving them viable for purposes of detection or assay.

Useful surface modifiers include fine-nanoscale gold; fine-nanoscale platinum; fine-nanoscale gold in combination with at least one metal oxide (preferably, titanium dioxide, ferric oxide, or a combination thereof); titanium dioxide; titanium dioxide in combination with at least one other (that is, other than titanium dioxide) metal oxide; ferric oxide; ferric oxide in combination with at least one other (that is, other than ferric oxide) metal oxide; and the like; and combinations thereof. Preferred surface modifiers include fine-nanoscale gold; fine-nanoscale platinum; fine-nanoscale gold in combination with at least ferric oxide or titanium dioxide; titanium dioxide; ferric oxide; titanium dioxide in combination with at least ferric oxide; and combinations thereof.

More preferred surface modifiers include fine-nanoscale gold; fine-nanoscale platinum; fine-nanoscale gold in combination with ferric oxide or titanium dioxide; titanium dioxide; titanium dioxide in combination with ferric oxide; ferric oxide; and combinations thereof (even more preferably, fine-nanoscale gold; fine-nanoscale gold in combination with ferric oxide or titanium dioxide; titanium dioxide in combination with ferric oxide; titanium dioxide; ferric oxide; and combinations thereof). Ferric oxide, titanium dioxide, and combinations thereof are most preferred.

At least some of the surface-modified diatomaceous earth concentration agents have zeta potentials that are at least somewhat more positive than that of untreated diatomaceous earth, and the concentration agents can be surprisingly significantly more effective than untreated diatomaceous earth in concentrating microorganisms such as bacteria, the surfaces of which generally tend to be negatively charged. Preferably, the concentration agents have a negative zeta potential at a pH of about 7 (more preferably, a zeta potential in the range of about −5 millivolts to about −20 millivolts at a pH of about 7; even more preferably, a zeta potential in the range of about −8 millivolts to about −19 millivolts at a pH of about 7;

most preferably, a zeta potential in the range of about −10 millivolts to about −18 millivolts at a pH of about 7).

The surface-modified diatomaceous earth concentration agents comprising fine-nanoscale gold or platinum can be prepared by depositing gold or platinum on diatomaceous earth by physical vapor deposition (optionally, by physical vapor deposition in an oxidizing atmosphere). As used herein, the term "fine-nanoscale gold or platinum" refers to gold or platinum bodies (for example, particles or atom clusters) having all dimensions less than or equal to 5 nanometers (nm) in size. Preferably, at least a portion of the deposited gold or platinum has all dimensions (for example, particle diameter or atom cluster diameter) in the range of up to (less than or equal to) about 10 nm in average size (more preferably, up to about 5 nm; even more preferably, up to about 3 nm).

In most preferred embodiments, at least a portion of the gold is ultra-nanoscale (that is, having at least two dimensions less than 0.5 nm in size and all dimensions less than 1.5 nm in size). The size of individual gold or platinum nanoparticles can be determined by transmission electron microscopy (TEM) analysis, as is well known in the art.

Diatomaceous earth (or kieselguhr) is a natural siliceous material produced from the remnants of diatoms, a class of ocean-dwelling microorganisms. Thus, it can be obtained from natural sources and is also commercially available (for example, from Alfa Aesar, A Johnson Matthey Company, Ward Hill, Mass.). Diatomaceous earth particles generally comprise small, open networks of silica in the form of symmetrical cubes, cylinders, spheres, plates, rectangular boxes, and the like. The pore structures in these particles can generally be remarkably uniform.

Diatomaceous earth can be used as the raw, mined material or as purified and optionally milled particles. Preferably, the diatomaceous earth is in the form of milled particles with sizes in the range of about 1 micrometer to about 50 micrometers in diameter (more preferably, about 3 micrometers to about 10 micrometers).

The diatomaceous earth can optionally be heat treated prior to use to remove any vestiges of organic residues. If a heat treatment is used, it can be preferable that the heat treatment be at 500° C. or lower, as higher temperatures can produce undesirably high levels of crystalline silica.

The amount of gold or platinum provided on the diatomaceous earth can vary over a wide range. Since gold and platinum are expensive, it is desirable not to use more than is reasonably needed to achieve a desired degree of concentration activity. Additionally, because nanoscale gold or platinum can be highly mobile when deposited using PVD, activity can be compromised if too much gold or platinum is used, due to coalescence of at least some of the gold or platinum into large bodies.

For these reasons, the weight loading of gold or platinum on the diatomaceous earth preferably is in the range of about 0.005 (more preferably, 0.05) to about 10 weight percent, more preferably about 0.005 (even more preferably, 0.05) to about 5 weight percent, and even more preferably from about 0.005 (most preferably, 0.05) to about 2.5 weight percent, based upon the total weight of the diatomaceous earth and the gold or platinum.

Gold and platinum can be deposited by PVD techniques (for example, by sputtering) to form concentration-active, fine-nanoscale particles or atom clusters on a support surface. It is believed that the metal is deposited mainly in elemental form, although other oxidation states may be present.

In addition to gold and/or platinum, one or more other metals can also be provided on the same diatomaceous earth supports and/or on other supports intermixed with the gold- and/or platinum-containing supports. Examples of such other metals include silver, palladium, rhodium, ruthenium, osmium, copper, iridium, and the like, and combinations thereof. If used, these other metals can be co-deposited on a support from a target source that is the same or different from the gold or platinum source target that is used. Alternatively, such metals can be provided on a support either before or after the gold and/or platinum is deposited. Metals requiring a thermal treatment for activation advantageously can be applied to a support and heat treated before the gold and/or platinum is deposited.

Physical vapor deposition refers to the physical transfer of metal from a metal-containing source or target to a support medium. Physical vapor deposition can be carried out in various different ways. Representative approaches include sputter deposition (preferred), evaporation, and cathodic arc deposition. Any of these or other PVD approaches can be used in preparing the concentration agents used in carrying out the process of the invention, although the nature of the PVD technique can impact the resulting activity. PVD can be carried out by using any of the types of apparatus that are now used or hereafter developed for this purpose.

Physical vapor deposition preferably is performed while the support medium to be treated is being well-mixed (for example, tumbled, fluidized, milled, or the like) to ensure adequate treatment of support surfaces. Methods of tumbling particles for deposition by PVD are described in U.S. Pat. No. 4,618,525 (Chamberlain et al.), the description of which is incorporated herein by reference. When carrying out PVD on fine particles or fine particle agglomerates (for example, less than about 10 micrometers in average diameter), the support medium is preferably both mixed and comminuted (for example, ground or milled to some degree) during at least a portion of the PVD process.

Physical vapor deposition can be carried out at essentially any desired temperature(s) over a very wide range. However, the deposited metal can be more active (perhaps due to more defects and/or lower mobility and coalescence) if the metal is deposited at relatively low temperatures (for example, at a temperature below about 150° C., preferably below about 50° C., more preferably at ambient temperature (for example, about 20° C. to about 27° C.) or less). Operating under ambient conditions can be generally preferred as being effective and economical, as no heating or chilling is required during the deposition.

The physical vapor deposition can be carried out in an inert sputtering gas atmosphere (for example, in argon, helium, xenon, radon, or a mixture of two or more thereof (preferably, argon)), and, optionally, the physical vapor deposition can be carried out in an oxidizing atmosphere. The oxidizing atmosphere preferably comprises at least one oxygen-containing gas (more preferably, an oxygen-containing gas selected from oxygen, water, hydrogen peroxide, ozone, and combinations thereof; even more preferably, an oxygen-containing gas selected from oxygen, water, and combinations thereof; most preferably, oxygen). The oxidizing atmosphere further comprises an inert sputtering gas such as argon, helium, xenon, radon, or a mixture of two or more thereof (preferably, argon). The total gas pressure (all gases) in the vacuum chamber during the PVD process can be from about 1 mTorr to about 25 mTorr (preferably, from about 5 mTorr to about 15 mTorr). The oxidizing atmosphere can comprise from about 0.05 percent to about 60 percent by weight oxygen-containing gas (preferably, from about 0.1 percent to about 50 percent by weight; more preferably, from about 0.5 percent to about 25 percent by weight), based upon the total weight of all gases in the vacuum chamber.

The diatomaceous earth support medium can optionally be calcined prior to metal deposition, although this can increase its crystalline silica content. Since gold and platinum are active right away when deposited via PVD, there is generally no need for heat treatment after metal deposition, unlike deposition by some other methodologies. Such heat treating or calcining can be carried out if desired, however, to enhance activity.

In general, thermal treatment can involve heating the support at a temperature in the range of about 125° C. to about 1000° C. for a time period in the range of about 1 second to about 40 hours, preferably about 1 minute to about 6 hours, in any suitable atmosphere such as air, an inert atmosphere such as nitrogen, carbon dioxide, argon, a reducing atmosphere such as hydrogen, and the like. The particular thermal conditions to be used can depend upon various factors including the nature of the support.

Generally, thermal treatment can be carried out below a temperature at which the constituents of the support would be decomposed, degraded, or otherwise unduly thermally damaged. Depending upon factors such as the nature of the support, the amount of metal, and the like, activity can be compromised to some degree if the system is thermally treated at too high a temperature.

The surface-modified diatomaceous earth concentration agents comprising metal oxide can be prepared by depositing metal oxide on diatomaceous earth by hydrolysis of a hydrolyzable metal oxide precursor compound. Suitable metal oxide precursor compounds include metal complexes and metal salts that can be hydrolyzed to form metal oxides. Useful metal complexes include those comprising alkoxide ligands, hydrogen peroxide as a ligand, carboxylate-functional ligands, and the like, and combinations thereof, Useful metal salts include metal sulfates, nitrates, halides, carbonates, oxalates, hydroxides, and the like, and combinations thereof.

When using metal salts or metal complexes of hydrogen peroxide or carboxylate-functional ligands, hydrolysis can be induced by either chemical or thermal means. In chemically-induced hydrolysis, the metal salt can be introduced in the form of a solution into a dispersion of the diatomaceous earth, and the pH of the resulting combination can be raised by the addition of a base solution until the metal salt precipitates as a hydroxide complex of the metal on the diatomaceous earth. Suitable bases include alkali metal and alkaline earth metal hydroxides and carbonates, ammonium and alkyl-ammonium hydroxides and carbonates, and the like, and combinations thereof. The metal salt solution and the base solution can generally be about 0.1 to about 2 M in concentration.

Preferably, the addition of the metal salt to the diatomaceous earth is carried out with stirring (preferably, rapid stirring) of the diatomaceous earth dispersion. The metal salt solution and the base solution can be introduced to the diatomaceous earth dispersion separately (in either order) or simultaneously, so as to effect a preferably substantially uniform reaction of the resulting metal hydroxide complex with the surface of the diatomaceous earth. The reaction mixture can optionally be heated during the reaction to accelerate the speed of the reaction. In general, the amount of base added can equal the number of moles of the metal times the number of non-oxo and non-hydroxo counterions on the metal salt or metal complex.

Alternatively, when using salts of titanium or iron, the metal salt can be thermally induced to hydrolyze to form the hydroxide complex of the metal and to interact with the surface of the diatomaceous earth. In this case, the metal salt solution can generally be added to a dispersion of the diatomaceous earth (preferably, a stirred dispersion) that has been heated to a sufficiently high temperature (for example, greater than about 50° C.) to promote the hydrolysis of the metal salt. Preferably, the temperature is between about 75° C. and 100° C., although higher temperatures can be used if the reaction is carried out in an autoclave apparatus.

When using metal alkoxide complexes, the metal complex can be induced to hydrolyze to form a hydroxide complex of the metal by partial hydrolysis of the metal alkoxide in an alcohol solution. Hydrolysis of the metal alkoxide solution in the presence of diatomaceous earth can result in metal hydroxide species being deposited on the surface of the diatomaceous earth.

Alternatively, the metal alkoxide can be hydrolyzed and deposited onto the surface of the diatomaceous earth by reacting the metal alkoxide in the gas phase with water, in the presence of the diatomaceous earth. In this case, the diatomaceous earth can be agitated during the deposition in either, for example, a fluidized bed reactor or a rotating drum reactor.

After the above-described hydrolysis of the metal oxide precursor compound in the presence of the diatomaceous earth, the resulting surface-treated diatomaceous earth can be separated by settling or by filtration or by other known techniques. The separated product can be purified by washing with water and can then be dried (for example, at 50° C. to 150° C.).

Although the surface-treated diatomaceous earth generally can be functional after drying, it can optionally be calcined to remove volatile by-products by heating in air to about 250° C. to 650° C. generally without loss of function. This calcining step can be preferred when metal alkoxides are utilized as the metal oxide precursor compounds.

In general, with metal oxide precursor compounds of iron, the resulting surface treatments comprise nanoparticulate iron oxide. When the weight ratio of iron oxide to diatomaceous earth is about 0.08, X-ray diffraction (XRD) does not show the presence of a well-defined iron oxide material. Rather, additional X-ray reflections are observed at 3.80, 3.68, and 2.94 Å. TEM examination of this material shows the surface of the diatomaceous earth to be relatively uniformly coated with globular nanoparticulate iron oxide material. The crystallite size of the iron oxide material is less than about 20 nm, with most of the crystals being less than about 10 nm in diameter. The packing of these globular crystals on the surface of the diatomaceous earth is dense in appearance, and the surface of the diatomaceous earth appears to be roughened by the presence of these crystals.

In general, with metal oxide precursor compounds of titanium, the resulting surface treatments comprise nanoparticulate titania. When depositing titanium dioxide onto diatomaceous earth, XRD of the resulting product after calcination to about 350° C. can show the presence of small crystals of anatase titania. With relatively lower titanium/diatomaceous earth ratios or in cases where mixtures of titanium and iron oxide precursors are used, no evidence of anatase is generally observed by X-ray analysis.

Since titania is well-known as a potent photo-oxidation catalyst, the titania-modified diatomaceous earth concentration agents of the present invention can be used to concentrate microorganisms for analysis and then optionally also be used as photoactivatable agents for killing residual microorganisms and removing unwanted organic impurities after use. Thus, the titania-modified diatomaceous earth can both isolate biomaterials for analysis and then be photochemically cleaned for re-use. These materials can also be used in filtration applications where microorganism removal as well as antimicrobial effects can be desired.

Preparation of Adsorption Buffer-Modified Inorganic Concentration Agent The adsorption buffer-modified inorganic concentration agent can be prepared by methods including a process comprising (a) contacting at least one of the above-described inorganic concentration agents with at least one cation-containing salt solution (preferably, aqueous), so as to wet at least a portion of the inorganic concentration agent and (b) drying the resulting at least partially wet inorganic concentration agent. Adsorption buffer solutions that are suitable for use as the cation-containing salt solution include those that comprise at least one monovalent or multivalent cation (preferably, at least one multivalent cation; more preferably, at least one divalent cation; most preferably, at least one divalent cation selected from divalent calcium cations, divalent magnesium cations, and combinations thereof). The cations are preferably metal cations, although other cations (for example, ammonium) can also be useful.

For example, useful adsorption buffers can comprise such salts as magnesium chloride ($MgCl_2$), calcium chloride ($CaCl_2$), magnesium sulfate ($MgSO_4$), calcium sulfate ($CaSO_4$), potassium chloride (KCl), sodium chloride (NaCl), potassium hydrogen phosphate ($K_2HPO_4$), ferrous chloride ($FeCl_2$), lanthanum chloride ($LaCl_3$), aluminum chloride ($AlCl_3$), and the like, and combinations thereof. The adsorption buffer solutions can be prepared by combining one or more salts with at least one solvent that is sufficiently polar to dissolve the salt(s). Preferably, the solvent is water. Dissolution of the salt(s) in the solvent can be facilitated by the addition of heat and/or by agitation or stirring, if desired. After dissolution, the resulting solution can be sterilized (preferably, by filter sterilization; more preferably, by filter sterilization using a standard microbiological filter having a pore size of about 0.22 micrometers).

The concentrations of the salts (in the solvent) can vary over a wide range, depending upon the nature of the salts and the solvents and upon the desired level of capture enhancement of the inorganic concentration agent, with concentrations of up to about 10 millimoles per liter (mM/L) (preferably, about 0.1 mM/L to about 5 mM/L) being typical. The pH of the salt solutions can range from about 6.0 to about 7.5, but relatively neutral pH values of about 6.5 to about 7.5 are generally preferred (more preferably, about 6.8 to about 7.3; more preferably, about 7.2).

Preferred adsorption buffers comprise at least one cation selected from magnesium cations ($Mg^{++}$), calcium cations ($Ca^{++}$), sodium cations ($Na^+$), potassium cations ($K^+$), ferrous cations ($Fe^{++}$), lanthanum cations ($La^{+++}$), aluminum cations ($Al^{+++}$), and combinations thereof (more preferably, at least one cation selected from magnesium cations, calcium cations, sodium cations, potassium cations, and combinations thereof; even more preferably, at least one cation selected from magnesium cations, calcium cations, potassium cations, and combinations thereof; most preferably, at least one cation selected from magnesium cations, calcium cations, and combinations thereof). An especially preferred adsorption buffer solution for use in the process of the invention comprises 5 mM KCl, 1 mM $CaCl_2$, 0.1 mM $MgCl_2$, and 1 mM $K_2HPO_4$ per liter of water and has a pH of 7.2.

The above-referenced step of contacting the inorganic concentration agent with adsorption buffer can be carried out by any of various known or hereafter-developed methods of providing contact between two materials, including those described below in the section concerning contacting the concentration agent with the sample. The amount of adsorption buffer that is used in the contacting can vary widely, depending upon the nature and amount of the inorganic concentration agent and the desired degree of capture enhancement. The amount of adsorption buffer solution can generally be sufficient to wet at least a portion of the inorganic concentration agent (for example, at least a portion of its exposed surface). Preferably, substantially all of the exposed surface of the inorganic concentration agent can be wetted (for example, when maximum capture enhancement is desired).

The contacting of the inorganic concentration agent with the adsorption buffer is preferably carried out by washing the agent with the buffer solution at least once (preferably, at least twice; more preferably, at least thrice). For example, such washing of an inorganic concentration agent can be effective to wet substantially all of the exposed surface of the inorganic concentration agent and can be carried out by immersing the agent in the buffer solution in a suitable container (for example, a test tube). The agent can be prewashed (for example, by rinsing with water), if desired, to remove impurities prior to contact with the buffer.

For example, washing can be effected by passing a particulate inorganic concentration agent at least once through a volume of buffer (for example, by relying upon gravitational settling over a period of, for example, about 10 minutes). Contact with the buffer can be enhanced by mixing (for example, by stirring, shaking, or use of a rocking platform) such that the particles of inorganic concentration agent repeatedly pass or settle through a substantial portion of the buffer. Mixing can be rapid such as by vortexing (for example, for one or two minutes at top speed) or can be achieved by gently tumbling the combination of particulate inorganic concentration agent and buffer in an "end over end" fashion (for example, by means of a device configured to hold a test tube or other type of reaction vessel and to slowly rotate the test tube or vessel in an "end over end" manner). Optionally, the inorganic concentration agent can be allowed to soak (for example, at ambient temperature) in the buffer for a desired period (for example, for a period of about 5 minutes after mixing).

Thus, in carrying out the washing of the inorganic concentration agent, mixing (for example, agitation, rocking, or stirring) and/or soaking are optional but preferred, in order to increase buffer contact with the concentration agent. One or more additives (for example, surfactants or wetting agents, dispersants, and the like) can be included in the combination of inorganic concentration agent and buffer (for example, to aid in dispersing and/or wetting of the agent), if desired.

After the contacting or washing step, the inorganic concentration agent preferably can be segregated (for example, by gravitational settling or by centrifugation or filtration; preferably, by centrifugation) and/or separated from the buffer (for example, by removal or separation of the resulting supernatant by decanting or siphoning, so as to leave the inorganic concentration agent at the bottom of the container or vessel utilized in carrying out the contacting step). The resulting at least partially wet inorganic concentration agent can then be dried either at ambient temperature (for example, about 23° C.) or at elevated temperature (for example, using an oven). Preferably, the drying is carried out at a temperature above about 25° C. (more preferably, at least about 50° C.; even more preferably, at least about 70° C.; most preferably, at least about 80° C.). The period of drying time can vary widely, depending upon, for example, the drying temperature that is utilized and the amount of the at least partially wet inorganic concentration agent (for example, about 1 gram of at least partially wet agent can be dried for about 48 hours or longer at ambient temperature, and about 5 grams of at least partially wet agent can be dried for about 5 or 6 hours at about 80° C.).

Sample

The concentration process of the invention can be applied to a variety of different types of samples, including, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility, an industrial facility, soil, a water source, a food preparation area (food contact and non-contact areas), a laboratory, or an area that has been potentially subjected to bioterrorism. Food processing, handling, and preparation area samples are preferred, as these are often of particular concern in regard to food supply contamination by bacterial pathogens.

Samples obtained in the form of a liquid or in the form of a dispersion or suspension of solid in liquid can be used directly, or can be concentrated (for example, by centrifugation) or diluted (for example, by the addition of a buffer (pH-controlled) solution). Samples in the form of a solid or a semi-solid can be used directly or can be extracted, if desired, by a method such as, for example, washing or rinsing with, or suspending or dispersing in, a fluid medium (for example, a buffer solution). Samples can be taken from surfaces (for example, by swabbing or rinsing). Preferably, the sample is a fluid (for example, a liquid, a gas, or a dispersion or suspension of solid or liquid in liquid or gas).

Examples of samples that can be used in carrying out the process of the invention include foods (for example, fresh produce or ready-to-eat lunch or "deli" meats), beverages (for example, juices or carbonated beverages), water (including potable water), and biological fluids (for example, whole blood or a component thereof such as plasma, a platelet-enriched blood fraction, a platelet concentrate, or packed red blood cells; cell preparations (for example, dispersed tissue, bone marrow aspirates, or vertebral body bone marrow); cell suspensions; urine, saliva, and other body fluids; bone marrow; lung fluid; cerebral fluid; wound exudate; wound biopsy samples; ocular fluid; spinal fluid; and the like), as well as lysed preparations, such as cell lysates, which can be formed using known procedures such as the use of lysing buffers, and the like. Preferred samples include foods, beverages, water, biological fluids, and combinations thereof (with foods, beverages, water, and combinations thereof being more preferred, and with water being most preferred).

Sample volume can vary, depending upon the particular application. For example, when the process of the invention is used for a diagnostic or research application, the volume of the sample can typically be in the microliter range (for example, 10 μL or greater). When the process is used for a food pathogen testing assay or for potable water safety testing, the volume of the sample can typically be in the milliliter to liter range (for example, 100 milliliters to 3 liters). In an industrial application, such as bioprocessing or pharmaceutical formulation, the volume can be tens of thousands of liters.

The process of the invention can isolate microorganisms from a sample in a concentrated state and can also allow the isolation of microorganisms from sample matrix components that can inhibit detection procedures that are to be used. In all of these cases, the process of the invention can be used in addition to, or in replacement of, other methods of microorganism concentration. Thus, optionally, cultures can be grown from samples either before or after carrying out the process of the invention, if additional concentration is desired.

Contacting

The process of the invention can be carried out by any of various known or hereafter-developed methods of providing contact between two materials. For example, the adsorption buffer-modified (or treated) concentration agent can be added to the sample, or the sample can be added to the concentration agent. A dipstick coated with concentration agent can be immersed in a sample solution, a sample solution can be poured onto a film coated with concentration agent, a sample solution can be poured into a tube or well coated with concentration agent, or a sample solution can be passed through a filter (for example, a woven filter) coated with concentration agent.

Preferably, however, the concentration agent and the sample are combined (using any order of addition) in any of a variety of containers (optionally but preferably, a capped, closed, or sealed container; more preferably, a capped test tube, bottle, or jar). Suitable containers for use in carrying out the process of the invention will be determined by the particular sample and can vary widely in size and nature. For example, the container can be small, such as a 10 microliter container (for example, a test tube) or larger, such as a 100 milliliter to 3 liter container (for example, an Erlenmeyer flask or a polypropylene large-mouth bottle). The container, the concentration agent, and any other apparatus or additives that contact the sample directly can be sterilized (for example, by controlled heat, ethylene oxide gas, or radiation) prior to use, in order to reduce or prevent any contamination of the sample that might cause detection errors. The amount of concentration agent that is sufficient to capture or concentrate the microorganisms of a particular sample for successful detection will vary (depending upon, for example, the nature and form of the concentration agent and sample volume) and can be readily determined by one skilled in the art. For example, 10 milligrams of concentration agent per milliliter of sample can be useful for some applications.

If desired, contacting can be effected by passing a particulate concentration agent at least once through a sample (for example, by relying upon gravitational settling over a period of, for example, about 10 minutes). Contact can be enhanced by mixing (for example, by stirring, shaking, or use of a rocking platform) such that the particles of concentration agent repeatedly pass or settle through a substantial portion of the sample. For small volumes on the order of microliters (typically less than 0.5 milliliter), mixing can be rapid such as by vortexing or "nutation," for example as described in U.S. Pat. No. 5,238,812 (Coulter et al.), the description of which is incorporated herein by reference. For larger volumes on the order of greater than or equal to 0.5 milliliters (typically 0.5 milliliter to 3 liters), mixing can be achieved by gently tumbling the particulate concentration agent and the sample in an "end over end" fashion, for example as described in U.S. Pat. No. 5,576,185 (Coulter et al.), the description of which is incorporated herein by reference. Such tumbling can be accomplished, for example, by means of a device configured to hold a test tube or other type of reaction vessel and to slowly rotate the test tube or vessel in an "end over end" manner. Contacting can be carried out for a desired period (for example, for sample volumes of about 100 milliliters or less, up to about 60 minutes of contacting can be useful; preferably, about 15 seconds to about 10 minutes or longer; more preferably, about 15 seconds to about 5 minutes).

Thus, in carrying out the process of the invention, mixing (for example, agitation, rocking, or stirring) and/or incubation (for example, at ambient temperature) are optional but preferred, in order to increase microorganism contact with the concentration agent. A preferred contacting method includes both mixing (for example, for about 15 seconds to about 5 minutes) and incubating (for example, for about 3 minutes to about 60 minutes) a microorganism-containing sample (preferably, a fluid) with particulate concentration agent. If desired, one or more additives (for example, lysis reagents, bioluminescence assay reagents, nucleic acid capture reagents (for example, magnetic beads), microbial growth media, buffers (for example, to moisten a solid sample), microbial staining reagents, washing buffers (for example, to wash away unbound material), elution agents (for example, serum albumin), surfactants (for example, Triton™ X-100 nonionic surfactant available from Union Carbide Chemicals and Plastics, Houston, Tex.), mechanical abrasion/elution agents (for example, glass beads), adsorption buffers (for example, the same buffer used for preparing the adsorption buffer-modified inorganic concentration agent or a different buffer), and the like) can be included in the combination of concentration agent and sample. Preferably, the sample contacting step is carried out without the inclusion of adsorption buffer as an additive in the combination of concentration agent and sample.

If desired, the concentration agent (alone or in combination with, for example, antimicrobial materials and/or with carrier materials in the form of liquids (for example, water or oils), solids (for example, fabrics, polymers, papers, or inorganic solids), gels, creams, foams, or pastes) can be applied to or rubbed against a non-porous or porous, solid, microorganism-contaminated or microorganism-contaminatable material or surface (for example, for use as a "cleaning" agent). Binders, stabilizers, surfactants, or other property modifiers can be utilized, if desired.

For such use, the concentration agent can be applied to woven or nonwoven fabrics and can be applied to disposable surfaces such as paper, tissues, cotton swabs, as well as to a variety of absorbent and nonabsorbent materials. For example, the concentration agent can be incorporated into cloth or paper carrier materials for use as "cleaning" wipes. The concentration agent can be applied (for example, in the form of wipes or pastes comprising a carrier material) to solid surfaces, for example, in home, day-care, industrial, and hospital settings, for cleansing toys, equipment, medical devices, work surfaces, and the like. When used for cleansing or other purposes, the sample can be simultaneously collected and contacted with the concentration agent in a single step, if desired.

Segregation and/or Separation

Optionally but preferably, the process of the invention further comprises segregation of the resulting microorganism-bound concentration agent. Such segregation preferably can be achieved by relying, at least in part, upon gravitational settling (gravity sedimentation; for example, over a time period of about 5 minutes to about 30 minutes). In some cases, however, it can be desirable to accelerate segregation (for example, by centrifugation or filtration) or to use combinations of any of the segregation methods.

The process of the invention can optionally further comprise separating the resulting microorganism-bound concentration agent and the sample. For fluid samples, this can involve removal or separation of the supernatant that results upon segregation. Separation of the supernatant can be carried out by numerous methods that are well-known in the art (for example, by decanting or siphoning, so as to leave the microorganism-bound concentration agent at the bottom of the container or vessel utilized in carrying out the process). Optionally, the bound microorganisms can be eluted or separated from the concentration agent (for example, chemically by using bovine serum albumin solutions or meat extract solutions, or physically by gentle sonication), if desired.

The process of the invention can be carried out manually (for example, in a batch-wise manner) or can be automated (for example, to enable continuous or semi-continuous processing).

Detection

A variety of microorganisms can be concentrated and, optionally but preferably, detected by using the process of the invention, including, for example, bacteria, fungi, yeasts, protozoans, viruses (including both non-enveloped and enveloped viruses), bacterial endospores (for example, *Bacillus* (including *Bacillus anthracis*, *Bacillus cereus*, and *Bacillus subtilis*) and *Clostridium* (including *Clostridium botulinum*, *Clostridium difficile*, and *Clostridium perfringens*)), and the like, and combinations thereof (preferably, bacteria, yeasts, viruses, bacterial endospores, fungi, and combinations thereof; more preferably, bacteria, yeasts, viruses, bacterial endospores, and combinations thereof; even more preferably, bacteria, viruses, bacterial endospores, and combinations thereof; still more preferably, gram-negative bacteria, gram-positive bacteria, non-enveloped viruses (for example, norovirus, poliovirus, hepatitis A virus, rhinovirus, and combinations thereof), bacterial endospores, and combinations thereof; most preferably, gram-negative bacteria, gram-positive bacteria, and combinations thereof). The process has utility in the detection of pathogens, which can be important for food safety or for medical, environmental, or anti-terrorism reasons. The process can be particularly useful in the detection of pathogenic bacteria (for example, both gram negative and gram positive bacteria), as well as various yeasts, molds, and mycoplasmas (and combinations of any of these).

Genera of target microorganisms to be detected include, but are not limited to, *Listeria*, *Escherichia*, *Salmonella*, *Campylobacter*, *Clostridium*, *Helicobacter*, *Mycobacterium*, *Staphylococcus*, *Shigella*, *Enterococcus*, *Bacillus*, *Neisseria*, *Shigella*, *Streptococcus*, *Vibrio*, *Yersinia*, *Bordetella*, *Borrelia*, *Pseudomonas*, *Saccharomyces*, *Candida*, and the like, and combinations thereof. Samples can contain a plurality of microorganism strains, and any one strain can be detected independently of any other strain. Specific microorganism strains that can be targets for detection include *Escherichia coli*, *Yersinia enterocolitica*, *Yersinia pseudotuberculosis*, *Vibrio cholerae*, *Vibrio parahaemolyticus*, *Vibrio vulnificus*, *Listeria monocytogenes* (for which *Listeria innocua* is a surrogate), *Staphylococcus aureus*, *Salmonella enterica*, *Saccharomyces cerevisiae*, *Candida albicans*, *Staphylococcal enterotoxin* ssp, *Bacillus cereus*, *Bacillus anthracis*, *Bacillus atrophaeus*, *Bacillus subtilis*, *Clostridium perfringens*, *Clostridium botulinum*, *Clostridium difficile*, *Enterobacter sakazakii*, *Pseudomonas aeruginosa*, and the like, and combinations thereof (preferably, *Staphylococcus aureus*, *Listeria monocytogenes* (for which *Listeria innocua* is a surrogate), *Escherichia coli*, *Pseudomonas aeruginosa*, and combinations thereof).

Microorganisms that have been captured or bound (for example, by adsorption) by the concentration agent can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample matrix components, staining, or the like.

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification), which is often a preferred method. The captured or bound microorganisms can be lysed to render their genetic material available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, and viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adenosine triphosphate (ATP) detection methods including those described in U.S. Pat. No. 7,422,868 (Fan et al.), the descriptions of which are incorporated herein by reference. Other luminescence-based detection methods can also be utilized.

Since the process of the invention is non-strain specific, it provides a general capture system that allows for multiple microorganism strains to be targeted for assay in the same sample. For example, in assaying for contamination of food samples, it can be desired to test for *Listeria monocytogenes*, *Escherichia coli*, and *Salmonella* all in the same sample. A single capture step can then be followed by, for example, PCR or RT-PCR assays using specific primers to amplify different nucleic acid sequences from each of these microorganism strains. Thus, the need for separate sample handling and preparation procedures for each strain can be avoided.

Diagnostic Kit

A diagnostic kit for use in carrying out the process of the invention comprises (a) an above-described adsorption buffer-modified inorganic concentration agent (preferably, particulate); (b) a testing container (preferably, a sterile testing container); and (c) instructions for using the concentration agent in carrying out the process of the invention. Preferably, the diagnostic kit further comprises one or more components selected from microorganism culture or growth media, lysis reagents, buffers, bioluminescence detection assay components (for example, luminometer, lysis reagents, luciferase enzyme, enzyme substrate, reaction buffers, and the like), genetic detection assay components, and combinations thereof. A preferred lysis reagent is a lytic enzyme supplied in a buffer, and preferred genetic detection assay components include one or more primers specific for a target microorganism.

For example, a preferred embodiment of the diagnostic kit of the invention contains a particulate adsorption buffer-modified inorganic concentration agent (for example, in a sterile disposable container such as a glass or polypropylene vial), in combination with instructions for using said agent in carrying out the process of the invention (for example, by mixing the concentration agent with a fluid sample to be analyzed, allowing the concentration agent to settle by gravity, removing the resulting supernatant, and detecting the presence of at least one concentration agent-bound target microorganism strain). The concentration agent optionally can be contained/aliquotted in a tear-open, sealed pouch to prevent contamination. The concentration agent can be in powder form. Preferably, the diagnostic kit comprises pre-measured aliquots (for example, based upon sample volume) of particulate adsorption buffer-modified inorganic concentration agent (more preferably, contained in one or more tear-open, sealed pouches).

EXAMPLES

Objects and advantages of this invention are further illustrated by the following examples, but the particular materials and amounts thereof recited in these examples, as well as other conditions and details, should not be construed to unduly limit this invention. All parts, percentages, ratios, and so forth, in the following examples are by weight, unless noted otherwise. All microorganism cultures were purchased from The American Type Culture Collection (ATCC; Manassas, Va.). Solvents and other reagents were obtained from Sigma-Aldrich Chemical Company, Milwaukee, Wis., unless specified differently.

Preparation of Surface-Modified Diatomaceous Earth Particulate Concentration Agents Kieselguhr (diatomaceous earth) was purchased from Alfa Aesar (A Johnson Matthey Company, Ward Hill, Mass.) as a white powder (325 mesh; all particles less than 44 micrometers in size). This material was shown by X-ray diffraction (XRD) to contain amorphous silica along with crystalline α-cristobalite and quartz.

Particulate concentration agents comprising two different surface modifiers (namely, titanium dioxide and ferric oxide) were prepared by surface treating the diatomaceous earth in the manner described below:

Deposition of Titanium Dioxide

A 20 weight percent titanium (IV) oxysulfate dehydrate solution was prepared by dissolving 20.0 g of $TiO(SO_4)$ .$2H_2O$ (Noah Technologies Corporation, San Antonio, Tex.) in 80.0 g of deionized water with stirring. 50.0 g of this solution was mixed with 175 mL of deionized water to form a titanium dioxide precursor compound solution. A dispersion of diatomaceous earth was prepared by dispersing 50.0 g of diatomaceous earth in 500 mL of deionized water in a large beaker with rapid stirring. After heating the diatomaceous earth dispersion to about 80° C., the titanium dioxide precursor compound solution was added dropwise while rapidly stirring over a period of about 1 hour. After the addition, the beaker was covered with a watch glass and its contents heated to boiling for 20 minutes. An ammonium hydroxide solution was added to the beaker until the pH of the contents was about 9. The resulting product was washed by settling/decantation until the pH of the wash water was neutral. The product was separated by filtration and dried overnight at 100° C.

A portion of the dried product was placed into a porcelain crucible and calcined by heating from room temperature to 350° C. at a heating rate of about 3° C. per minute and then held at 350° C. for 1 hour.

Deposition of Iron Oxide

Iron oxide was deposited onto diatomaceous earth using essentially the above-described titanium dioxide deposition process, with the exception that a solution of 20.0 g of $Fe(NO_3)_3.9H_2O$ (J. T. Baker, Inc., Phillipsburg, N.J.) dissolved in 175 mL of deionized water was substituted for the titanyl sulfate solution. A portion of the resulting iron oxide-modified diatomaceous earth was similarly calcined to 350° C. for further testing.

Materials 18 megaohm water: 18 megaohm sterile deionized water obtained by using a Milli-Q™ Gradient deionization system from Millipore Corporation, Bedford, Mass.

3M™ Petrifilm™ Aerobic Count Plates (flat film culture devices comprising dry, rehydratable culture medium) were obtained from 3M Company, St. Paul, Minn.

3M™ Petrifilm™ *E. coli*/Coliform Count Plates (flat film culture devices comprising at least one fermentable nutrient) were obtained from 3M Company, St. Paul, Minn.

Adsorption buffer: a cation-containing salt solution having a pH of 7.2 produced by mixing 5 mM KCl, 1 mM $CaCl_2$, 0.1 mM $MgCl_2$, and 1 mM $K_2HPO_4$ in one liter of 18 megaohm water (with magnetic stirring) and then filter sterilizing the solution by passing it through a VWR™ Vacuum Filtration System with a 0.22 micrometer nylon filter membrane (obtained from VWR, West Chester, Pa.).

100× adsorption buffer: a cation-containing salt solution having a pH of 7.2 produced by mixing equal amounts of (1) a filter-sterilized (essentially as described above) solution of 500 mM KCl, 100 mM $CaCl_2$, and 10 mM $MgCl_2$, in 100 mL of 18 megaohm water and (2) a filter-sterilized (essentially as described above) solution of 100 mM $K_2HPO_4$ in 100 mL of 18 megaohm water (all solutions prepared with magnetic stirring).

Amine-functionalized (organic coating from reaction with amine-functional organosilane) glass beads having a size range of 30-50 microns were obtained from PolySciences, Inc., Warrington, Pa.

CM-111: amorphous, spheroidized magnesium silicate; microspheres shaped as solid spheres with particle density of 2.3 g/cc; surface area of 3.3 $m^2$/g; particle size: 90 percent less than about 11 microns, 50 percent less than about 5 microns, 10 percent less than about 2 microns; obtained as 3M™ Cosmetic Microspheres CM-111 from 3M Company, St. Paul, Minn.

Fe-DE: ferric oxide deposited onto diatomaceous earth essentially as described above.

Ti-DE: titanium dioxide deposited onto diatomaceous earth essentially as described above.

W-210: alkali alumino silicate ceramic; microspheres shaped as solid spheres with particle density of 2.4 g/cc; surface area of 5 $m^2$/cc; particle size: 95 percent less than about 12 microns, 90 percent less than about 9 microns, 50 percent less than about 3 microns, 10 percent less than about 1 micron; obtained as 3M™ Ceramic Microspheres W-210 from 3M Company, St. Paul, Minn.

Examples 1-4 and Comparative Examples C-1-C-6

Preparation of Adsorption Buffer-Modified Inorganic Concentration Agents

An aliquot of 5 grams of CM-111 powder was divided into two portions, and the portions were placed in two 50 mL polypropylene centrifuge tubes and suspended/dispersed in 50 mL 18 megaohm sterile water by vortexing for 10 seconds at 14,000 revolutions per minute (rpm; top speed) on a VWR Analog Vortex Mixer (VWR, West Chester, Pa.). The resulting suspensions was then centrifuged at 3000 rpm for 5 minutes (Eppendorf centrifuge 5804, VWR, West Chester, Pa.) to obtain pelleted CM-111. Each pellet was then washed again by resuspending in 50 mL 18 megaohm water and processing essentially as described above. This step of prewashing the CM-111 was carried out again for a total of three washings in 50 mL of 18 megaohm water. Next, the resulting prewashed CM-111 pellets were dispersed in 50 mL volumes of adsorption buffer by vortexing essentially as described above and then centrifuging essentially as described above to obtain pelleted CM-111. This step of washing the CM-111 in 50 mL of adsorption buffer was performed three times. After the last wash, the resulting supernatant was discarded, and the resulting at least partially wet pellets were placed on sterile glass petridishes (VWR, West Chester, Pa.). The at least partially wet pellets were dried at 80° C. (using a Robbins Scientific Model 400 Hybridization Incubator available from SciGene, Sunnyvale, Calif.) for 5-6 hours (Example 1). The resulting dried powders (adsorption buffer-modified inorganic concentration agent) were stored at room temperature (about 23° C.).

The following other inorganic concentration agents, in 100 milligram amounts, were treated using essentially the same process (100 mg of agent washed three times in 50 mL of 18 megaohm water and then washed three times in 50 mL of adsorption buffer): Ti-DE (Example 2), Fe-DE (Example 3), amine-functionalized glass beads (Comparative Example C-6), and W-210 (Example 4). The corresponding untreated agents were retained for comparison: untreated CM-111 (Comparative Example C-1), untreated Ti-DE (Comparative Example C-2), untreated Fe-DE (Comparative Example C-3), untreated amine-functionalized glass beads (Comparative Example C-4), and untreated W-210 (Comparative Example C-5).

Concentration of Microorganism-Containing Samples

A loopful (standard four millimeter bacteriological loop) of overnight streaked culture of E. coli (ATCC 51813) from a Tryptic Soy Agar plate (4 weight percent (wt %) Difco™ Tryptic Soy Broth, Becton Dickinson, Sparks, Md.) was used to make a 0.5 McFarland standard (Vitek DENSICHEK, bioMerieux, Inc., Durham, N.C.) in 3 mL Butterfield's Buffer (pH 7.2, VWR, West Chester, Pa.). This standard corresponded to ~$10^8$ colony forming units/mL (CFU/mL). Serial dilutions were made in filter-sterilized (essentially as described above) deionized 18 megaohm water. A 1:1000 further dilution from a $10^5$ CFU/mL dilution was carried out in 15 mL of filter-sterilized 18 megaohm water, resulting in a final concentration of about 100 CFU/mL. Particulate inorganic concentration agents (treated (Examples 1-5) and untreated (Comparative Examples C-1-C-5)) were weighed in 5 mL polypropylene tubes (BD Falcon, VWR, West Chester, Pa.) and tested for bacterial capture using 10 mg of concentration agent in a 1.0 mL volume of 100 CFU/mL test sample. The tubes were then capped and their contents mixed by shaking manually at room temperature (23° C.) for about 1 minute.

After mixing, the tubes were incubated for 15 minutes on a Thermolyne Vari Mix™ rocking platform (Barnstead International, Iowa, 14 cycles/minute). After the incubation, the tubes were set on the bench top for 10 minutes to settle the particulate concentration agent. After settling, 1 mL of the resulting supernatant was removed using a pipette and plated on 3M™ Petrifilm™ Aerobic Count Plate (3M Company, St. Paul, Minn.). The settled pellets were resuspended in 1.0 mL water and plated similarly.

A 1:1000 dilution from the initial $10^5$ CFU/mL dilution (without particulate concentration agent) was plated as a control on 3M™ Petrifilm™ Aerobic Count Plate (3M Company, St. Paul, Minn.). The particulate concentration agents (having no sample contact) were also plated as sterility controls. The resulting plates were incubated overnight in a 37° C. incubator (VWR Orbital Shaking Incubator, VWR, West Chester. Pa.).

Per the manufacturer's instructions, the plates were analyzed by using a 3M™ Petrifilm™ Plate Reader (PPR, 3M Company, St. Paul; automated optical detection system) and colony counts were obtained. Results were calculated using the following formula:

Capture Efficiency=(Number of Colonies on Concentration Agent/Total Number of Colonies in Control)×100

The results (mean and standard deviation for 2 data points) are shown in Table 1 below. In the concentration agent descriptions in Table 1 and subsequent tables, "AB-washed" is used to indicate that the concentration agent had been treated with adsorption buffer.

TABLE 1

| Example No. | Concentration Agent | Capture Efficiency (percent) | Standard Deviation |
|---|---|---|---|
| C-1 | CM-111 | 72 | 7 |
| 1 | AB-washed CM-111 (dried 80° C.) | 99 | 0 |
| C-2 | Ti-DE | 33 | 2 |
| 2 | AB-washed Ti-DE | 56 | 8 |
| C-3 | Fe-DE | 31 | 5 |
| 3 | AB-washed Fe-DE | 46 | 5 |
| C-4 | Amine-functionalized Glass Beads | 7.5 | 5 |

TABLE 1-continued

| Example No. | Concentration Agent | Capture Efficiency (percent) | Standard Deviation |
|---|---|---|---|
| C-6 | AB-washed Amine-functionalized Glass Beads | 1.9 | 1 |
| C-5 | W-210 | 13 | 5 |
| 4 | AB-washed W-210 | 38 | 7 |

Comparative Examples C-7-C-10

Separate 100 mg aliquots of powders (inorganic concentration agents Ti-DE (Comparative Example C-7), Fe-DE (Comparative Example C-8), W-210 (Comparative Example C-9), and CM-111 (Comparative Example C-10)) were processed essentially as described in Examples 1-4 above, except that after the last spin/wash step, the resulting at least partially wet powders were not dried but were used as wet pellets by resuspending the pellets in 1 mL adsorption buffer. Capture efficiency testing with ~100 CFUs E. coli in 1 mL spiked water was carried out essentially as described in Examples 1-4. The results (mean and standard deviation for 2 data points) are shown in Table 2 below.

TABLE 2

| Example No. | Concentration Agent | Capture Efficiency (percent) | Standard Deviation |
|---|---|---|---|
| C-7 | Ti-DE | 37 | 9 |
| C-8 | Fe-DE | 41 | 8 |
| C-9 | W-210 | 60 | 3 |
| C-10 | CM-111 | 18 | 6 |

Example 5 And Comparative Example C-11

A separate CM-111 pellet was treated essentially as in Example 1, but instead of drying the pellet at 80° C., it was resuspended in adsorption buffer, and the resulting slurry was dried at room temperature (about 23° C.) for 48 hours (Example 5). Capture efficiency testing with approximately 100 CFUs E. coli in 1.1 mL spiked water was carried out essentially as described in Examples 1-4. The results (mean and standard deviation for 2 data points) are shown in Table 3 below.

TABLE 3

| Example No. | Concentration Agent | Capture Efficiency (percent) | Standard Deviation |
|---|---|---|---|
| C-1 | CM-111 | 72 | 7 |
| 1 | AB-washed CM-111 dried at 80° C. | 99 | 0 |
| 5 | AB-washed CM-111 dried at 23° C. | 86 | 4 |

An untreated aliquot of the CM-111 lot used for the room temperature drying experiment was retained for surface composition determination (Comparative Example C-11).

Surface Composition Determination by Elemental Surface Chemical Analysis (ESCA)

The surface compositions of adsorption buffer-treated and untreated (comparative) concentration agents were analyzed by X-ray photoelectron spectroscopy (XPS; also known as ESCA). Aliquots of the powders were pressed onto double-sided, pressure sensitive adhesive tapes on aluminum foil. Excess powder was removed from each sample surface by blowing with compressed nitrogen gas.

Spectral data was acquired using a Kratos AXIS Ultra™ DLD spectrometer (Kratos Analytical, Manchester, England) having a monochromatic Al—Kα X-ray excitation source (1487 eV) and a hemispherical electron energy analyzer operated in a constant pass energy mode. The emitted photoelectrons were detected at a take-off angle of 90 degrees measured with respect to the sample surface with a solid angle of acceptance of ±10 degrees. A low-energy electron flood gun was used to minimize surface charging. Measurements were made using a 140 Watt power to anode and $2 \times 10^{-8}$ Torr chamber pressure.

An area of the surface of each concentration agent aliquot measuring about 300 micrometers by about 700 micrometers was analyzed for each data point. Three areas on each aliquot were analyzed and averaged to obtain the reported average atomic percent values. Data processing was carried out using standard Vision2™ software (Kratos Analytical, Manchester, England). Data was collected for Examples 1-5 and for Comparative Examples C-1-C-6 and C-11. Results (elements present at a detectable level by XPS on the surface of the concentration agents; reported numbers are averaged over 3 data points) are shown in Table 4 below:

TABLE 4

| Example No. | Concentration Agent | Metal:Si Ratio (Metal = Mg + Ca + K) |
|---|---|---|
| C-2 | Ti-DE | 0.054 |
| 2 | AB-washed Ti-DE | 0.085 |
| C-3 | Fe-DE | 0.032 |
| 3 | AB-washed Fe-DE | 0.063 |
| C-5 | W-210 | 0.103 |
| 4 | AB-washed W-210 | 0.189 |
| C-4 | Amine-functionalized Glass Beads | 0.191 |
| C-6 | AB-washed Amine-functionalized Glass Beads | 0.172 |
| C-11 | CM-111 control for 23° C. | 0.118 |
| 5 | AB-washed CM-111 dried at 23° C. | 0.285 |
| C-1 | CM-111 control for 80° C. | 0.130 |
| 1 | AB-washed CM-111 dried at 80° C. | 0.533 |

Example 6 And Comparative Examples C-12-C-13

An isolated *E. coli* (ATCC 51813) colony was inoculated from a streak plate into 5 mL BBL™ Trypticase™ Soy Broth (Becton Dickinson, Sparks, Md.) and incubated at 37° C. for 18-20 hours. This overnight culture at ~$10^9$ colony forming units/mL was diluted in Butterfield's Buffer (pH 7.2, VWR, West Chester, Pa.). A 1:1000 dilution from a $10^2$ bacteria/mL dilution was carried out in 100 mL of potable water, resulting in *E. coli*-spiked water having a final concentration of 0.1 CFU/mL (10 CFUs total). For Comparative Example C-12, 100 mg of untreated/control CM-111 was added to sterile 250 mL polypropylene conical bottom centrifuge tubes (VWR, West Chester, Pa.) containing 100 mL of *E. coli*-spiked water. For Comparative Example C-13, 100 mg of untreated/control CM-111 was added to sterile 250 mL polypropylene conical bottom centrifuge tubes (VWR, West Chester, Pa.) containing 100 mL of *E. coli*-spiked water and 1.1 mL of 100× adsorption buffer. For Example 6, 100 mg of CM-111 that had been adsorption buffer modified essentially as in Example 1 was added to sterile 250 mL polypropylene conical bottom centrifuge tubes (VWR, West Chester, Pa.) containing 100 mL of *E. coli*-spiked water. The tubes were capped and were then incubated at room temperature (23° C.) for 60 minutes on a Thermolyne Vari Mix™ rocking platform (Barnstead International, Iowa, 14 cycles/minute). After the incubation, the tubes were allowed to stand on the lab bench for 30 minutes to settle the CM-111 particles.

In the CM-111 retrieval step, an 80 mL volume of the resulting supernatant was discarded by pipetting, and the remaining 20 mL containing the settled particles was pipetted out of the tubes, transferred to a 50 mL sterile polypropylene tube (VWR, West Chester, Pa.), and spun down at 2000 rpm for 5 minutes (Eppendorf centrifuge 5804, VWR, West Chester, Pa.) to obtain pellets. The pellets were resuspended in 1 mL Butterfield's Buffer and inoculated onto 3M™ Petrifilm™ *E. coli*/Coliform Count Plates. A 1 mL volume from the ~$10^2$ CFU/mL dilution (without particulate concentration agent) was plated as a control, in duplicate, on 3M™ Petrifilm™ *E. coli*/Coliform Count Plates (3M Company, St. Paul, Minn.). The resulting plates were further processed per the manufacturer's instructions and analyzed using a 3M™ Petrifilm™ Plate Reader (3M Company, St. Paul, Minn.). Results (averaged over 2 data points) are shown in Table 5.

TABLE 5

| Example No. | Concentration Agent | *E. coli* Challenge in 100 mL Water (CFUs) | *E. coli* Recovered on Concentration Agent (CFUs) | Capture Efficiency (percent) |
|---|---|---|---|---|
| C-12 | CM-111 (untreated) | 13 | 1 | 8 |
| C-13 | CM-111 (untreated but with liquid 100X adsorption buffer added) | 13 | 13 | 100* |
| 6 | Adsorption Buffer-Modified CM-111 | 13 | 15 | 115** |

*standard deviation of ~20 percent
**standard deviation of ~10 percent

Example 7 and Comparative Examples C-14-C-16

An isolated *E. coli* (ATCC 51813) colony was inoculated from a streak plate into 5 mL BBL Trypticase Soy Broth (Becton Dickinson, Sparks, Md.) and incubated at 37° C. for 18-20 hours. This overnight culture at ~$10^9$ colony forming units/mL was diluted in filter-sterilized 18 megaohm water. A 1:1000 dilution from a $10^6$ bacteria/mL dilution was carried out in 10 mL of filter-sterilized 18 megaohm water, resulting in *E. coli*-spiked water having a final concentration of ~$10^3$ bacteria/mL (~$10^4$ CFUs total). For Example 7, 10 mg of adsorption buffer modified (essentially as in Example 1) CM-111 was added to sterile 50 mL polypropylene conical bottom centrifuge tubes (VWR, West Chester, Pa.) containing 10 mL of *E. coli*-spiked water. The tubes were capped and were then incubated at room temperature (23° C.) for 30 minutes on a Thermolyne Vari Mix™ rocking platform (Barnstead International, Iowa, 14 cycles/minute). After the incubation, the tubes were centrifuged for 5 minutes at 2000 rpm (Eppendorf centrifuge 5804, VWR, West Chester, Pa.) to settle CM-111 particles and thereby form CM-111 pellets.

Control tubes containing 100 microliters unspiked water (one tube) and 100 microliters *E. coli*-spiked water (two tubes, each from a different dilution), respectively, without CM-111 concentration agent were capped and incubated similarly (Comparative Examples C-14 (unspiked), C-15 (Dilution No. 1: 100 microliters of $10^3$ CFUs/mL dilution), and C-16 (Dilution No. 2: 100 microliters of $10^5$ CFUs/mL dilution)). As a plating control, an adsorption buffer modified (essentially as in Example 1) CM-111 pellet (with captured bacteria) was plated on 3M™ Petrifilm™ Aerobic Count Plates. The resulting plates were further processed per the manufacturer's instructions and analyzed using a 3M™ Petrifilm™ Plate Reader (3M Company, St. Paul., Minn.). The results from this plating control indicated a concentration of $1.9 \times 10^3$ CFUs/mL for Comparative Example C-15. The CM-111 plating control exhibited a capture efficiency of 100 percent.

The CM-111 pellets were resuspended in 100 microliters 18 megaohm water and transferred to sterile 1.5 mL polypropylene microfuge tubes (PLASTIBRAND™, BRAND GMBH+CO, Wertheim, Germany). A volume of 100 microliters BacTiter-Glo™ ATP assay reagent (Promega, Madison, Wis.) was added to each tube (including the control tubes) and mixed for 15 seconds at 14,000 rpm (top speed) on a VWR Analog Vortex Mixer (VWR, West Chester, Pa.). Bioluminescence (of the control tubes and the CM-111 pellet-containing tubes) was measured (in Relative Luciferase Units (RLUs)) using a benchtop luminometer (FB-12 single tube luminometer, Berthold Detection Systems USA, Oak Ridge, Tenn.). Results (mean from two data points) are summarized in Table 6 below.

TABLE 6

| Example No. | Sample/ Concentration Agent | ATP Signal (RLUs) | ATP Signal Normalized to Unspiked Water (RLUs) | Percent Normalized Signal |
| --- | --- | --- | --- | --- |
| C-14 | Unspiked Water/ No CM-111 | 5,424 | 0 | 0 |
| C-16 | Spiked Water (Dilution No. 2)/ No CM-111 | 26,468 | 21,044 | 100 |
| C-15 | Spiked Water (Dillution No. 1)/ No CM-111 | 7,022 | 1598 | 8 |
| 7 | Spiked Water/ Adsorption Buffer-Modified CM-111 | 22,733 | 17,309 | 82 |

RLU = Relative Luciferase Units.

Examples 8-12 and Comparative Examples C-17-C-22

A loopful (standard four millimeter bacteriological loop) of overnight growth of *Staphylococcus aureus* (ATCC 6538) was used to make McFarland standards of 0.5 (corresponding to ~$10^8$ CFU/mL), which were tested with 10 mg of various different particulate concentration agents prepared essentially as described above. The various particulate concentration agents (10 mg) were tested for capture of ~100 CFUs from 1.1 mL water samples essentially as described in Examples 1-4 and were plated on 3M™ Petrifilm™ Aerobic Count Plates (3M Company, St. Paul, Minn.). A 1 mL volume from the ~$10^2$ CFU/mL dilution (without particulate concentration agent) was plated as a control, in duplicate, on 3M™ Petrifilm™ Aerobic Count Plates (3M Company, St. Paul, Minn.). The plates were analyzed using a 3M™ Petrifilm™ Plate Reader (3M Company, St. Paul., Minn.).

Capture data for *S. aureus* is shown in Table 7 below (mean and standard deviation for 2 data points are given). When the microorganism colonies and the concentration agent were similar in color (providing little contrast for the plate reader), results were based upon the supernatant and were then reported in terms of percent capture of microorganisms by the concentration agent using the formulas below:

Percent CFU/mL in Supernatant=(number of colonies from plated supernatant)/(number of colonies from plated untreated control sample)×100

Capture Efficiency or Percent Capture=100−Percent CFU/mL in Supernatant

Capture efficiencies calculated from the above equations based on the supernatant are labeled "Supernatant" under "Test Method" in Table 7. Capture efficiencies based on the concentrations agents were based on the equation given in Examples 1-4 and are labeled as "Agent" under "Test Method" in Table 7.

TABLE 7

| Example No. | Concentration Agent | Test Method | Capture Efficiency (percent) | Standard Deviation |
| --- | --- | --- | --- | --- |
| C-17 | CM-111 | Supernatant | 60 | 5 |
| 8 | AB-washed CM-111 (dried at 23° C.) | Supernatant | 87 | 0 |
| 9 | AB-washed CM-111 (dried at 80° C.) | Supernatant | 99 | 0 |
| C-18 | Ti-DE | Supernatant | 37 | 3 |
| 10 | AB-washed Ti-DE | Supernatant | 66 | 4 |
| C-19 | Fe-DE | Supernatant | 53 | 12 |
| 11 | AB-washed Fe-DE | Supernatant | 39 | 10 |
| C-20 | Amine-functionalized Glass Beads | Agent | 2 | 0 |
| C-21 | AB-washed Amine-functionalized Glass Beads | Agent | 2 | 2 |
| C-22 | W-210 | Agent | 38 | 1 |
| 12 | AB-washed W-210 | Agent | 17 | 2 |

Examples 13-16 and Comparative Examples C-23-C-26

A loopful (standard four millimeter bacteriological loop) of overnight growth of *Pseudomonas aeruginosa* (ATCC 15442) from Tyrptic Soy Agar plates (4 weight percent Difco™ Tryptic Soy Broth, Becton Dickinson and Company, Sparks, Md.; prepared according to manufacturer's instructions) was used to make McFarland standards of 0.5 (corresponding to ~$10^8$ CFU/mL), which were tested with 10 mg of various different particulate concentration agents prepared essentially as described above. The various particulate concentration agents (10 mg) were tested for capture of ~100 CFUs from 1.0 mL water samples essentially as described in Examples 1-4 and were plated on 3M™ Petrifilm™ Aerobic Count Plates (3M Company, St. Paul, Minn.). A 1 mL volume from the initial $10^2$ CFUs/mL dilution (without concentration agent) was plated as a control, in duplicate, on 3M™ Petrifilm™ Aerobic Count Plates (3M Company, St. Paul, Minn.). The resulting plates were incubated at 37° C. for about 24 hours and were analyzed using a 3M™ Petrifilm™ Plate Reader (PPR, 3M Company, St. Paul). The capture efficiencies of the particulate agents were determined by using the formula described in Examples 1-4. Capture data for *P. aeruginosa* is shown in Table 8 below (mean and standard deviation for 2 data points).

TABLE 8

| Example No. | Concentration Agent | Capture Efficiency (percent) | Standard Deviation |
|---|---|---|---|
| C-23 | CM-111 | 26 | 1 |
| 13 | AB-washed CM-111 | 49 | 0 |
| C-24 | Ti-DE | 5 | 1 |
| 14 | AB-washed Ti-DE | 12 | 4 |
| C-25 | Fe-DE | 8 | 1 |
| 15 | AB-washed Fe-DE | 4 | 2 |
| C-26 | W210 | 5 | 2 |
| 16 | AB-washed W-210 | 8 | 1 |

Examples 17-21 and Comparative Examples C-27-C-32

A loopful (standard four millimeter bacteriological loop) of overnight growth of *Listeria innocua* (ATCC 33090) from a Blood Agar plate (5 percent Blood Agar from Hardy Diagnostics, Santa Maria, Calif.) was used to make McFarland standards of 0.5 (corresponding to ~$10^8$ CFUs/mL), which were tested with 10 mg of various different particulate concentration agents prepared essentially as described above. The particulate concentration agents (10 mg) were tested for capture of ~100 CFUs from 1.0 mL water samples essentially as described in Examples 1-4. After 10 minutes of settling, the resulting 1 mL supernatants were removed into separate 5 mL sterile tubes. The resulting pellets of concentration agent were resuspended in 100 microliters 18 megaohm water and plated by spreading on MOX plates (Modified Oxford Medium Plates, Hardy Diagnostics, Santa Maria, Calif.). A volume of 100 microliters from the supernatants was also plated similarly. A 1:10 dilution from the initial ~$10^2$ CFUs/mL dilution (without concentration agent) was plated, in duplicate, as a control. Colony counts were obtained by manual counting, and capture efficiencies of the particulate concentration agents were determined by using the formula described above in Examples 1-4. Capture data for *L. innocua* is shown in Table 9 below (mean and standard deviation for 2 data points).

TABLE 9

| Example No. | Concentration Agent | Capture Efficiency (percent) | Standard Deviation |
|---|---|---|---|
| C-27 | Ti-DE | 21 | 0 |
| 17 | AB-washed Ti-DE | 14 | 5 |
| C-28 | Fe-DE | 17 | 0 |
| 18 | AB-washed Fe-DE | 17 | 5 |
| C-29 | Amine-functionalized Glass Beads | 2.0 | 2 |
| C-30 | AB-washed Amine-functionalized Glass Beads | 0.0 | 0 |
| C-31 | W-210 | 3.5 | 5 |
| 19 | AB-washed W-210 | 3.5 | 5 |
| C-32 | CM-111 | 33 | 4 |
| 20 | AB-washed CM-111 (dried at 23° C.) | 63 | 4 |
| 21 | AB-washed CM-111 (dried at 80° C.) | 66 | 9 |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

I claim:

1. A process for concentrating at least one microorganism strain comprising (a) providing an adsorption buffer-modified inorganic concentration agent disposed in a sterile container, said adsorption buffer-modified inorganic concentration agent comprising at least one cation-containing salt dried on the inorganic concentration agent, said adsorption buffer-modified inorganic concentration agent being prepared by a process comprising (1) contacting at least one inorganic concentration agent with at least one cation-containing salt solution, so as to wet at least a portion of said inorganic concentration agent and (2) drying the resulting at least partially wet inorganic concentration agent; (b) providing a sample comprising at least one microorganism strain; (c) contacting said adsorption buffer-modified inorganic concentration agent, thereby concentrating at least one microorganisms strain, with said sample such that at least a portion of said at least one microorganism strain is bound to or captured by said adsorption buffer-modified inorganic concentration agent, wherein said inorganic concentration agent is selected from amorphous metal silicates and combinations thereof; and (d) (1) segregating the resulting microorganism-bound, adsorption buffer-modified inorganic concentration agent, (2) separating the resulting segregated microorganism-bound, adsorption buffer-modified inorganic concentration agent from said sample, and/or (3) detecting the presence of at least one bound microorganism strain.

2. The process of claim 1, wherein said inorganic concentration agent is amorphous, spheroidized magnesium silicate.

3. The process of claim 1, wherein said cation-containing salt solution is aqueous.

4. The process of claim 1, wherein said cation-containing salt solution comprises at least one cation selected from magnesium cations, calcium cations, sodium cations, potassium cations, ferrous cations, lanthanum cations, aluminum cations, and combinations thereof.

5. The process of claim 1, wherein said cation-containing salt solution comprises at least one multivalent cation.

6. The process of claim 5, wherein said multivalent cation is a divalent cation.

7. The process of claim 6, wherein said divalent cation is selected from divalent calcium cations, divalent magnesium cations, and combinations thereof.

8. The process of claim 1, wherein said cation-containing salt solution comprises 5 mM KCl, 1 mM $CaCl_2$, 0.1 mM $MgCl_2$, and 1 mM $K_2HPO_4$ per liter of water and has a pH of 7.2.

9. The process of claim 1, wherein said contacting of said inorganic concentration agent with said cation-containing salt solution is carried out by washing.

10. The process of claim 1, wherein said drying is carried out by heating said at least partially wet inorganic concentration agent to a temperature above about 25° C.

11. The process of claim 1, wherein said sample is in the form of a fluid.

12. The process of claim 1, wherein said microorganism strain is selected from strains of bacteria, fungi, yeasts, protozoans, viruses, bacterial endospores, and combinations thereof.

13. The process of claim 1, wherein said contacting of said adsorption buffer-modified inorganic concentration agent with said sample is carried out by mixing said adsorption buffer-modified inorganic concentration agent and said sample.

14. A process for concentrating at least one microorganism strain comprising (a) providing an adsorption buffer-modified inorganic concentration agent disposed in a sterile container, said adsorption buffer-modified inorganic concentration agent comprising at least one cation-containing salt dried on the inorganic concentration agent, said adsorption buffer-modified inorganic concentration agent being prepared by a process comprising treating at least one silicon-containing inorganic concentration agent with at least one adsorption buffer comprising at least one cation, so as to provide silicon-containing inorganic concentration agent having a surface composition having a ratio of atoms of said at least one cation to atoms of silicon that is greater than that of the corresponding untreated silicon-containing inorganic concentration agent, as determined by X-ray photoelectron spectroscopy (XPS); (b) providing a sample comprising at least one microorganism strain; (c) contacting said adsorption buffer-modified inorganic concentration agent with said sample such that at least a portion of said at least one microorganism strain is bound to or captured by said adsorption buffer-modified inorganic concentration agent thereby concentrating at least one microorganism strain; and (d) (1) segregating the resulting microorganism-bound, adsorption buffer-modified inorganic concentration agent, (2) separating the resulting segregated microorganism-bound, adsorption buffer-modified inorganic concentration agent from said sample, and/or (3) detecting the presence of at least one bound microorganism strain.

15. The process of claim 1, wherein said cation-containing salt solution comprises a concentration of said cation-containing salt of about 0.1 millimoles per liter to about 5 millimoles per liter.

* * * * *

UNITED STATES PATENT AND TRADEMARK OFFICE
CERTIFICATE OF CORRECTION

PATENT NO. : 9,029,100 B2  
APPLICATION NO. : 13/511169  
DATED : May 12, 2015  
INVENTOR(S) : Manjiri Kshirsagar Page 1 of 1

It is certified that error appears in the above-identified patent and that said Letters Patent is hereby corrected as shown below:

In the claims

Column 30,  
Line 28, in claim 1, after "agent," delete "thereby concentrating at least one microorganisms strain," and insert the same after "agent," on Col. 30, line 31.

Signed and Sealed this  
First Day of March, 2016

Michelle K. Lee  
*Director of the United States Patent and Trademark Office*